United States Patent [19]

Smith et al.

[11] Patent Number: 5,597,599

[45] Date of Patent: Jan. 28, 1997

[54] METHOD FOR PROCESSING A PERISHABLE PRODUCT

[75] Inventors: Brian S. Smith; Kenneth W. McMillin; John H. Wells; A. James Farr, all of Baton Rouge, La.; Jerry L. Mitchell, Livingston, Tex.

[73] Assignees: Pakor, Inc., Livingston, Tex.; Louisiana State University and Agricultural College, Baton Rouge, La.

[21] Appl. No.: 323,439

[22] Filed: Oct. 4, 1994

Related U.S. Application Data

[63] Continuation-in-part of Ser. No. 880,869, May 11, 1992, Pat. No. 5,352,467, which is a continuation-in-part of Ser. No. 510,987, Apr. 19, 1990, abandoned, which is a continuation of Ser. No. 214,195, Jun. 27, 1988, Pat. No. 4,919,955, which is a division of Ser. No. 94,384, Sep. 8, 1987, abandoned.

[51] Int. Cl.$^6$ ........................................................ B65B 31/04
[52] U.S. Cl. ........................... 426/316; 53/434; 53/512; 426/320; 426/326; 426/392
[58] Field of Search .................................. 426/316, 320, 426/326, 335, 392, 418; 53/432, 434, 512

[56] References Cited

U.S. PATENT DOCUMENTS

| | | | |
|---|---|---|---|
| 3,897,210 | 7/1975 | Gruber et al. | 426/320 X |
| 4,744,199 | 5/1988 | Gannon | 53/434 |
| 5,352,467 | 10/1994 | Mitchell et al. | 426/316 |

*Primary Examiner*—Leo B. Tentoni
*Attorney, Agent, or Firm*—Sankey & Luck, L.L.P.

[57] ABSTRACT

A method of preservation and presentation including the steps of positioning a perishable product having a significant porosity and permeability into a gas impermeable package in the presence of a first agent, thereafter sealing the product in the package in the presence of the agent under a positive pressure and maintaining gas communication between the product and the first agent for a time necessary for the concentration of the first agent to be reduced by 50%.

26 Claims, No Drawings

METHOD FOR PROCESSING A PERISHABLE PRODUCT

CROSS REFERENCES TO RELATED APPLICATIONS

This application is a continuation-in-part of applicant's application Ser. No. 07/880,869 filed May 11, 1992, now U.S. Pat. No. 5,352,467, which was a continuation-in-part of application Ser. No. 510,947 filed Apr. 19, 1990, now abandoned, which was a continuation of application Ser. No. 214,195, filed Jun. 27, 1988, now U.S. Pat. No. 4,919,955, which was a divisional of application Ser. No. 94,384, filed Sep. 8, 1987 now abandoned. The disclosure of the aforementioned applications is herein incorporated by reference.

BACKGROUND OF THE INVENTION

1. Field of the Invention

The present invention relates to a method for enhancing the marketable characteristics of a given product, and especially a perishable product, by exposing said product to one or more selected agents (e.g., a liquid, vapor, aerosol, or gas) in a predetermined, sequential order of delivery and exposure, while said product is maintained within a sealed consumer-ready package. More specifically, the present invention relates to an in situ method for processing a perishable product, where said method contemplates the employment of one or more chemical agents specifically selected for use with a given product, where said agent(s) are applied to the product while it is maintained within a sealed gas impermeable container, where further said agent(s) are employed at a selected concentration, temperature, pressure, and for a time sufficient to establish a predetermined modification of the particular product for retail presentation.

2. Description of the Prior Art

Perishable products, specifically meat, poultry, or fish products, are generally washed and packaged in bulk at a slaughter house or other processing facility preparatory to shipment to various retail outlets. These products are commonly packaged in containers such as plastic wrapped trays, pouches of plastic, paper or plastic coated paper bags, food storage tubes and the like. Upon reaching the retail outlet, the products are sorted, cut or otherwise handled for repackaging into containers that are typically pliant relative to rigid cans, bottles and cans in that they are flexible or soft to the touch. These containers are frequently transparent, as in the case of meats and poultry, to enable retail customers to view the product. Such products, especially meats, are commonly packaged in the ambient atmosphere naturally occurring at such facilities.

Packaging of perishable products in such a fashion, however, ordinarily results in a fairly rapid reduction of the quality of the product as the product begins to age on the shelf with a resultant unacceptable appearance, smell and taste associated with bacterial, chemical or biochemical deterioration. This phenomena occurs, though at a slower pace, even when such products are maintained in a refrigerated condition.

Product spoilage is partially a result of the multiplication of bacteria introduced onto the surface of the product during processing. Contamination of this sort is particularly pronounced in the processing of poultry. Moreover, the atmosphere introduced into the container of all perishable products also contributes to spoilage since such atmosphere contains a variety of airborne bacteria. Bacterial deterioration is also enhanced by "cross contamination" which is often brought about as a result of the common handling of products by human or mechanized devices during the packaging stage.

The rate and extent of lipid oxidation, color degradation, bacterial growth, texture changes and dehydration determines in large part the shelf life of the product. In this connection, a perishable product is generally considered to have a shelf life determined by the amount of time necessary for the deterioration to reach proportions which render the product unfit for consumption. This shelf life varies depending on the product and the conditions under which the product is processed and packaged. Fish and poultry traditionally have very short shelf lives when stored in an unfrozen state, whereas the shelf life for meat is generally somewhat longer. Regardless of the type of product, however, the presence of certain bacteria, especially the pathogenic bacteria, can render the product dangerous for consumption even when present in small amounts. As a result of the above described problems relating to bacterial growth and other deteriorative changes, perishable products are generally refrigerated or frozen to enhance their shelf life.

A lowering in temperature is effective to retard the deterioration in the quality of the produce since lipid oxidation, color degradation, bacterial growth, and texture deterioration are slowed. For this reason, a perishable product generally will not spoil if frozen, but will almost immediately spoil if stored at room temperature in the absence of preservatives. However, even under frozen conditions, other quality properties other than microbiological deterioration may be sacrificed and thus render the product less usable after storage.

A number of techniques have evolved to utilize the benefits of freezing. One commercial preservation and storage method involves subjecting various products, especially fish and poultry, to temperatures slightly below 32° F. (0° C.). This technique, often referred to as "crusting", literally involves the freezing of the outer layer of water in the product. Products subject to this technique are "slacked out" and displayed for sale in a refrigerated, non-frozen state. Bulk retail and institutional packages of various perishable products are sometimes handled in this fashion.

Some products, however, and especially poultry products, are felt to deteriorate in quality once subjected to freezing. Additionally, it is often times undesirable to freeze a product if further processing is contemplated at a secondary processing facility. For these reasons, other techniques have been developed to store or transport the product while maintaining the product at temperatures above freezing.

One such technique is vacuum packaging. Vacuum packaging inhibits bacterial growth by removing the operative oxygen environment necessary to sustain aerobic growth. Disadvantages with vacuum packaging, however, include the purplish color induced in meat products which often times diminishes the appearance of such products for purposes of retail sale. Vacuum packaging also results in the creation of an undesirable liquid exudate which is caused by package pressure differential. If commercial sale of vacuum packed products is desired, the product also must often be removed from the vacuum package and exposed to oxygen so that the meat may "bloom." When exposed to oxygen, however, surface bacterial derived from the processing or packaging operation, previously kept in check by vacuum packaging, are then able to multiply and soon begin to move the product toward spoilage.

Other non-frozen techniques involves packing the product in a carbon dioxide atmosphere. A $CO_2$ atmosphere, like the vacuum pack, also inhibits the growth of aerobic bacteria. Thus the product, when exposed to an aerobic environment, begins to rapidly degrade as a result of residual bacterial. Additionally, the product often absorbs the $CO_2$, thus creating a negative pressure differential within the package and thereby making the package prone to collapse.

The above described techniques are useful, therefore, only from the standpoint of marginally prolonging the life of a perishable product during shipping, or when it is otherwise possible to maintain an anaerobic environment around the product. Moreover, these techniques fail to inhibit the growth of anaerobic bacteria and do not maintain other desired quality characteristics important in retail sale.

Ozone ($O_3$) has long been widely used as an oxidizing agent for bacterial, virus, and mold control for meat and fish storage, fresh fish processing, produce storage, restaurants, cooling towers, animal feed products, marine life, beverage containers, swimming pools, potable water systems, and tertiary waste systems. Ozone is also currently widely used for odor control in air conditioning systems, industrial processing operations, restaurants, mortuaries, rest homes and other applications. Ozone gas is a very strong oxidizing agent, having an oxidation potential more than twice that of chlorine and approximately three times that of hydrogen peroxide. Ozone also has the advantage of breaking down upon use as an oxidant into oxygen, which is normally beneficial. The use of ozone for the sterilization or preservation of food products is generally described in U.S. Pat. No. 4,549,477 ("the '477 patent), which discloses both the historical applications (batch process) as well as the application of ozone in a continuous process whereby the perishable product is moved through a treatment zone filled with ozone.

Disadvantages associated with the techniques described in the '477 patent includes the possibility of recontamination of the product after it is moved out of the ozone flushed region and into a packaging area. This possibility of contamination is enhanced if the product is not already positioned in the package but must be positioned either mechanically or manually. Further, the aforedescribed processes do not allow for the possible retention of the activity of the agent to be maintained by confinement to the smaller space involved with a product in a retail package.

SUMMARY OF THE INVENTION

The present invention addresses the above noted and other disadvantages by providing a method to substantially modify a given product once it is sealed within a consumer-ready package. With specific regard to perishable products, the present invention presents the advantage of enabling the non-frozen shelf life of a perishable product to be significantly enhanced. In this connection, the method of the present invention enables the storage of products for a longer time at a given temperature above those ordinarily believed necessary to prevent spoilage.

The method of the present invention also contemplates the processing of a varied range of products, specifically perishable products, so as to enhance their color, smell, texture, appearance and other such characteristics while the products are maintained within a sealed or a selectively permeable container.

In a general aspect of the invention, a method is provided whereby a product, specifically including a perishable product, is selectively exposed to one or more agents for a time calculated to product a predetermined change in the appearance and physical character of the product. This exposure is preferably conducted in an ordered, sequential fashion beginning with exposure of the product to a first agent at the time it is first sealed within the package and ultimately modified or removed during the time the product is transported and ultimately presented to the consumer.

More specifically, the present invention is directed to an in situ method of processing a produce, specifically including a perishable product, within a gas-tight, consumer-ready package, which method comprises first subjecting the product to an atmosphere containing one or more chemical agent(s), where such agent(s) are selected to have a maximum beneficial end result on each given product, and where such agent(s) are applied in a selected order, and at selected concentrations, pressures and temperatures. These variables for the application of specific agents for the most part depend on the physical nature of the product itself, e.g., the type of product, its moisture, fat content and structural configuration. The method of the present invention extends the products' shelf life by substantially reducing the microbial activity on the surface of the product. Alternatively, or additionally, the method of the invention may enhance such aesthetic characteristics of the product such as color, smell or taste as indicated above.

In another embodiment of the invention, a non-compressed, non-compacted food product is sealed in a gas impermeable package in contact with a first agent, where the concentration of the first agent is determined by the type and the amount of the product. In this embodiment, it is contemplated that the first agent includes a strong oxidant, e.g., ozone, where further the first agent may be replaced by a second agent, e.g., ascorbic acid.

The method of the present invention presents a number of advantages over the art. With respect to perishable products, one such advantage is the ability to significantly reduce or eliminate the number of aerobic and anaerobic micro organisms present on the surface of such a product after the product has been sealed within a container. In such a fashion, the shelf life of the product can be substantially increased. Further, since the product remains in the sealed package, there is little possibility of recontamination. Moreover, since the product is treated in situ in the consumer-ready package, lower concentrations of the chemical agent are required to produce a desired treatment. In such a fashion, waste of the costly enhancement agents can be minimized. Moreover, when the present method is used in combination with conventional preservation techniques such as freezing, an even greater shelf life may be realized.

Further, the elimination or substantial reduction in the number of surface bacteria resultant from the present method allows for the storage of some perishable products for extended periods of time without the need for refrigeration. This is beneficial in remote areas of the world in the event that refrigeration facilities are unavailable or temporarily disabled.

The present invention also provides for means to alter other aesthetic characteristics, e.g. color, texture, smell, of a given product so as to enhance its appeal upon presentation to the consumer.

Other objects and advantages of the invention will become apparent form the following detailed description of the preferred embodiment.

DETAILED DESCRIPTION OF THE PREFERRED EMBODIMENT

In one preferred embodiment of the present invention, a given product, e.g., a beef product, is prepared for shipment to a retail facility, e.g., a grocery facility, for ultimate presentation to the consumer. For obvious reasons, it is desired to maintain the maximum freshness of the meat product during the time it is transported from the slaughterhouse to the retail outlet. In such a fashion the product is afforded a maximum shelf life.

The first step of such a method is to seal the product in a fluid tight container while the product is exposed to an oxidizer, e.g., $O_3$, $F_2$, $H_2O_2$, $KMnO_4$, HOBr, HOCl, $Cl_2$, $ClO_2$, $O_2$, $Br_2$ or $I_2$. By exposure to one or a combination of such oxidizers, the microbial presence on the exterior of the product will be substantially reduced or even neutralized. Moreover, by sealing both the oxidizer and the product within the container, the residence time of the oxidizer defined as the half life or the amount of time necessary for the concentration of the oxidizer, or some other agent, to be reduced by 50% may be strictly controlled.

To enhance the effectiveness of the oxidizer, it may be desirable, once the package is sealed, to introduce a higher concentration of the same or a different agent into the sealed package. To further enhance the effectiveness of such an oxidizer, it may also be desirable to change the pressure within the package beyond a single atmosphere. Still alternatively, it may be desirable to change the temperature of the meat product and thereby expedite the oxidation process within the sealed package. In still a further embodiment, it may also be desirable to employ infrared or ultraviolet radiation to said product to inhibit microbial activity on a given product.

To ensure that the product is uniformly exposed to a given agent, e.g., an oxidizer, the package preferably includes a bottom tray which is provided with a series of raised knobs or ridges. To further ensure that the product receives maximum exposure to the agent, the package, once sealed, may also be vibrated or oscillated for a short period of time during the packaging or transport stage, so as to vary the contact zones between the raised knobs or ridges and the product. In this connection, exposure to a selected agent is maximized when the product has a significant void fraction and a sufficient permeability therethrough so as to allow for gas communication with a high proportion of the product surface area.

While exposure of the product to an oxidizer is beneficial from the standpoint of eliminating most surface microbial activity, it is sometimes desirable to remove or reduce the oxidizer after a selected residence time. The length of this residence time will depend on such factors as the nature of the product, the mass of the product, the fat content of the product, the water content of the product, the temperature at which the product has been maintained, and the identity and concentration of the oxidizer. Once this residence time has been achieved, it is desirable to externally activate or remove the oxidizer from the package without disrupting the sealed integrity of the package itself. This may be achieved by extracting the oxidizer through a septum valve or other similar resealable valve disposed in the package.

Once the oxidizing agent is withdrawn, it may be desirable to introduce a second agent into the package to further minimize microbial activity on the product, or to inhibit the growth of bacteria during product presentation. These agents may include a $CO_2$ content. Alternatively, an agent with an $O_2$ content may be preferred. Oxygen causes the meat product to "bloom", or assume a bright red color. This bright red color is generally indicative of the freshness of the meat product and is therefore desirable to the consumer. Other agents contemplated within the scope of the invention include nitrogen, argon, carbon dioxide, hydrogen, krypton, neon, helium, xenon, and mixtures thereof.

Multiple variations of the above described technique may be employed with any number of different perishable products. For example, if it is desired to process a perishable fish or poultry product, it may be necessary to alter the above method to change the concentration of the agent and/or the residence time. Further, in the case of fish or poultry products, which tend to degrade at a much faster rate than do meat products, there is necessarily an increased emphasis on inhibiting bacterial growth during transportation and storage or the product preparatory to retail sale. Hence, it may be desirable to maintain a weak oxidizer within the package during the transportation and storage phases.

Aside from the above described deteriorative effects associated with bacterial spoilage, perishable products including beef products may often adopt a color, odor or texture which does not accurately reflect their freshness and fitness for consumption. Consequently, the sale of such products is often inhibited as a result of such aesthetic characteristics. It may therefore be desirable to treat these products with yet another independent agent which, while it has no appreciable effect on the spoilage of the product, serves to enhance the characteristics usually deemed important for retail presentation and consumption of such. Such agents may include ascorbic acid, isoascorbic acid, erythorbic acid, lactic acid, citric acid, succinic acid or mixtures of salts thereof. Alternatively, other agents such as glycerol monolaurate, sodium sorbate, sodium acetate, sodium iodoacetate, potassium sorbate, potassium acetate, potassium iodoacetate, iodoacetomide or mixtures or acidic solutions thereof may also be used.

In yet another embodiment of the present invention, a loosely packed highly porous perishable product is positioned in a gas impermeable tray in gas communication with a first agent. In this context, "loosely packed" is defined as including optimal spacing between individual particles so as to allow substantial gaseous access to the product surface and/or as including a significant void space within the product mass. It is further desirable that the particular food product not undergo external compression and/or compaction upon loading into the package so as to maintain both high porosity and permeability.

The product is then sealed in the package under a positive pressure. The purpose of the positive pressure is to compel gas communication between the food product and the first agent. The term "positive pressure" as used herein denotes any measurable internal package pressure greater than the external atmosphere pressure on the package but not so great as to compress the product so as to decrease either its porosity or permeability.

The first agent contemplated for use with this embodiment includes such agents as $O_3$, $F_2$, $KMnO_4$, HClO, $ClO_2$, $O_2$, $Br_2$ or $I_2$. The concentration of the first agent is determined by the degree of effectiveness desired by exposure, the compositional characteristics of the product, e.g., moisture content, fat content, protein content and ash content, and the amount of the product being treated. For example, a higher percentage of a stronger agent may be desired with a fresh poultry or fish product as opposed to a weaker oxidizer for use with a grain or rice product.

As earlier described, it may be desirable in some instances to introduce a second agent into the sealed package for the purposes of enhancing the overall aesthetic characteristics of the product. It is desirable that such second agent be introduced as a vapor or an aerosol and be drawn from the group consisting of ascorbic acid, isoascorbic acid, erythorbic acid, lactic acid, citric acid, succinic acid or mixtures of salts thereof.

To allow extended distribution and storage time, it may be desirable in some instances to introduce yet a third agent into gas communication with a food product. To facilitate introduction and/or subsequent extraction of the agent, it is again desirable that the third agent be introduced in gaseous or aerosol form. It is envisioned that the third agent be drawn from a group comprising glycerol monolaurate, sodium sorbate, sodium acetate, sodium iodoacetate, potassium sorbate, potassium acetate, potassium iodoacetate, iodoacetomide or mixtures or acidic solutions thereof.

In a complementary embodiment, ozone may be used to facilitate tenderness in whole muscle meat and poultry cuts and to reduce the inconsistency of the tenderness between various muscles and cuts of meat and poultry. Alternatively, ozone may be used in conjunction with nitrogen and carbon dioxide for the purpose of forming a chemically stable, cured meat color.

EXAMPLE I

Ground beef trimmings (80/20) of normal pH (5.5 to 5.8) are chilled to 38° F. within 24 hours of slaughter and coarsely ground (¼" plate), mixed, and finely ground (⅛" plate). The extruded or ground product is discharged onto a conveyor belt moving at the same speed as the product flow from the grinder or extruder so that the density or compaction of the product stream is not changed. A portion sizer is used divide the product stream into 1.5 lb. sections before the product is mechanically loaded into pre-formed polystyrene barrier MAP trays with no change in the natural shape, density or porosity of the product from that as it exited the grinder. The filled trays enter a packager where the chamber is evacuated before introduction of air containing ozone at 20 ppm into the chamber. After a dwell exposure or resident time of 15 seconds for contact between the ground beef and ozonated air, the air is evacuated and the chamber is filled with a gas mixture of 80% nitrogen and 20% carbon dioxide. The package is sealed with impermeable lidding film such that the nitrogen and carbon dioxide mixture remains inside the package during distribution and storage. The treatment of ozone completely permeates the ground beef to induce microbial inhibition and improve textural properties.

EXAMPLE II

Turkeys are conventionally slaughtered and the carcasses chilled to 40° before hand-deboning of breasts. Breasts from 6 pounds to 12 pounds are stuffed into impermeable heat-sealed bags and water-cooked to no less than 160° F. Upon removal from the steam-heated water baths, the packages of breasts are chilled to 38° F. in a continuous mechanical brine chiller. Upon exit from the chiller, bags are manually opened and breasts are placed on conveyor belts to automatic slicing equipment, slices of 1/16 inch thickness and weighing ½ to 2 ounces are placed into impermeable film-lined plastic trays. The trays are conveyed into a chamber which is evacuated before introduction of an aerosol of 1% glycerol monolaurate and 1% sodium sorbate. After an exposure time of 3 minutes between the aerosol and the product, the chamber is evacuated and a mixture of 20% oxygen, 25% carbon dioxide and 55% nitrogen is introduced into the package immediately before heat-sealing of barrier lidding film to the tray. The treatment of this aerosol inhibits mold growth and induces maintenance of a whiter, less green color to the turkey breast slices.

EXAMPLE III

Chicken carcasses are automatically deboned and skin removed to yield 2 to 3 pounds of edible muscle. The white breast portions are separated form dark breast muscle portions by line workers on each side of a conveyor belt. The white meat is conveyed into a mechanical dicer which reduces the particle size to ⅜ inch or less cubes. The cubes are conveyed into a tunnel for steam cooking to an internal temperature of no less than 165° F. before being blast chilled to 40° F. Approximately ¾ to 1 pound of chicken cubes are mechanically loaded into trays with an inner lining of impermeable film. The trays are placed into packaging equipment where, inside a chamber, the cubes are exposed to 500 ppm citric acid vapor for 30 seconds. After re-evacuation of the chamber to remove the citric acid vapor before the trays are heat-sealed with barrier film. The citric acid treatment serves to improve the shelf-life of cooked poultry by reducing lipid instability and breakdown.

EXAMPLE IV

Dry (less than 14% moisture) rough or unmilled rice is shelled to result in brown rice with adhering bran coat. Two pounds of the brown rice is packaged in a gas-impermeable rigid canister, evacuated, and back-flushed with an aerosol containing 0.5% concentration of ascorbic acid. Prior to sealing the canister of rice, a pressurized gas mixture of 50% nitrogen 50% carbon dioxide is added to the canister without removal of the first ascorbic acid aerosol. The final pressure within the canister is adjusted to 20 pounds absolute (PSIA) per square inch atmospheric pressure. The package brown rice is stored in ambient conditions without refrigeration. The packaging method illustrated extends the usable shelf life of the brown rice by denaturing the native enzyme lipase which normally would catalyze hydrolyric oxidation of the lipids within the rice bran and suppress microbial growth which would normally occur during room temperature storage without acid treatment.

Yet another embodiment of the present invention includes a method of product preservation comprising the steps of positioning a perishable product in a selectively gas permeable package in the presence of a first gas, sealing the package with a positive package pressure, inclosing the first package in a larger package, chamber or enclosure with a higher positive pressure such that gaseous or aerosol agents within the larger container diffuse from the larger enclosure into the first package so as to enhance the appearance, organoleptic or shelf life characteristics of the perishable product.

EXAMPLE V

Retail salad mix is prepare by washing lettuce before mechanical cutting into pieces of less than 2-inch length, washing carrots before mechanical shredding into slivers of less than ¼ inch diameter, and washing red cabbage which is mechanically chopped into cubes of less than ¾ inch before combining each of the ingredients in a 6:2:1 by weight proportion of lettuce, carrots and cabbage, respectively. Two pounds of salad mix is placed in a gas-impermeable semi-rigid tray. Before package closure, 0.1% erythorbic acid is introduced into contact with the salad mix and the package is heat-sealed with a lidding film permeable to carbon dioxide. A multiple of 12 trays containing salad mix are placed into an outer cardboard carton lined with a gas-impermeable liner. Prior to sealing the outer carton and liner, a pressurized gas mixture of 80% carbon dioxide and 20% nitrogen is inserted into the atmosphere surrounding the trays containing the salad mix. The final pressure within the outer carton is adjusted to 16 psi. The carton containing packages of salad mix are maintained under refrigeration conditions of 33° to 45° F. The use of erythorbic acid prevents discoloration (browning) of the salad mix, reduces vegetable tissue respiration by transpiration of the carbon dioxide into the packages at a fixed rate, and prevents deterioration by tissue dehydration thorough the impermeable nature of the master package lined carton.

Although particular detailed embodiments of the method of the invention have been described therein, it should be understood that the invention is not restricted to the details of the preferred embodiments. Many changes in design, composition, configuration and dimensions are possible without departing from the spirit and scope of the instant invention.

Further benefits and advantages of the present invention will become obvious to those skilled in the art in light of the following claims.

What is claimed is:

1. A method for processing a perishable product comprising the steps of:

positioning a perishable product having a high porosity and permeability in a gas impermeable package such that a substantial portion of the product is in gas communication with a selected first agent; and thereafter sealing such product in said package for a selected resident time such that gas communication with said product and said first agent is maintained, where the type and concentration of said first agent is determined by the compositional characteristics of said product.

2. The method of claim 1 wherein said first agent is drawn from a group consisting of $O_3$, $F_2$, $H_2O_2$, $KMnO_4$, $HClO$, $ClO_2$, $O_2$, $Br_2$ and $I_2$.

3. The method of claim 2 wherein the resident time for said first agent is defined as the half life, or amount of time necessary for the concentration of the first agent to be reduced to 50% of the initial amount of the first agent.

4. The method of claim 1 where the compositional characteristics include the moisture content, fat content, protein content and ash content of the product.

5. The method of claim 1 wherein the container is sealed so as to maintain a positive pressure inside said container vis-a-vis the exterior of said chamber.

6. The method of claim 5 wherein said positive pressure is greater than that pressure exerted on the exterior to said container but not so great as to significantly increase the density of said product.

7. The method of claim 1 further including the step of introducing a second agent into gas communication with said product so as to effect the appearance, organoleptic and shelf life traits of said product.

8. The method of claim 7 wherein said second agent is introduced as a vapor or an aerosol.

9. The method of claim 7 wherein said second agent is drawn from a group consisting of ascorbic acid, isoascorbic acid, erythorbic acid, lactic acid, citric acid, succinic acid and mixtures of and salts thereof.

10. The method of claim 7 further including the step of introducing yet a third agent into gas communication with said product.

11. The method of claim 10 wherein said third agent is introduced as a vapor or as an aerosol.

12. The method of claim 8 wherein said third agent is drawn from a group consisting of glycerol monolaurate, sodium sorbate, sodium acetate, sodium iodacetate, potassium sorbate, potassium acetate, potassium iodecetate, iodoacetomide and mixtures and acidic solutions thereof.

13. The method of claim 1 further including the step of replacing said first agent with a second agent preliminary to sealing said package.

14. The method of claim 13 wherein said second agent is drawn from a group consisting of nitrogen, oxygen, argon, carbon dioxide, hydrogen, krypton, neon, helium, xenon and mixtures thereof.

15. The method of claim 1 wherein said first agent comprises a mixture of ozone, nitrogen and carbon dioxide so as to induce a chemically stable, cured pigment form in meat, poultry and seafood.

16. A method of processing a perishable product comprising the steps of:

positioning a particulated perishable product having a significant void fraction and a significant permeability therethrough so as to allow for gas communication with a high proportion of the product surface area;

exposing said product to a first agent for a resident time adequate to alter the external appearance, organoleptic or shelf life traits of said product; and sealing said product in a gas impermeable package with said first agent under a positive pressure.

17. The method of claim 16 wherein said first agent is drawn from a group consisting of $O_3$, $F_2$, $H_2O_2$, $KMnO_4$, $HClO$, $ClO_2$, $O_2$, $Br_2$ and $I_2$.

18. The method of claim 16 further including the step of introducing a second agent into said sealed package in gas communication with said product.

19. The method of claim 18 wherein said second agent is drawn from the group consisting of ascorbic acid, isoascorbic acid, erythorbic acid, lactic acid, citric acid, succinic acid and mixtures of salts thereof.

20. The method of claim 18 further including the step of introducing yet a third agent into said sealed package into gas communication with said product.

21. The method of claim 20 wherein said third agent is drawn from a group consisting of glycerol monolaurate, sodium sorbate, sodium acetate, sodium iodoacetate, potassium sorbate, potassium acetate, potassium iodoacetate, iodoacetomide and mixtures and acidic solutions thereof.

22. The method of claim 16 further including the step of replacing said first agent with a second agent and thereafter sealing said package with a positive pressure.

23. The method of claim 22 wherein said second agent is drawn from a group consisting of nitrogen, oxygen, argon, carbon dioxide, hydrogen, krypton, neon, helium, xenon and mixtures thereof.

24. A method of processing a perishable product comprising the steps of positioning a perishable product in a selectively permeable package under a selected pressure;

enclosing said permeable package in a chamber containing a first agent;

creating a higher pressure in said chamber than is present in said package so as to induce said agent in said chamber to diffuse into the package.

25. The method of claim 24 wherein said first agent is drawn from a group consisting of $O_3$, $F_2$, $H_2O_2$, $KMnO_4$, $HOBr$, $HClO$, $O_2$, $Br_2$ and $I_2$.

26. The method of claim 24 wherein the concentration of the first agent is determined by the moisture content, fat content, protein content or ash content of said product.

* * * * *